United States Patent
Brackett et al.

(10) Patent No.: US 6,859,288 B1
(45) Date of Patent: Feb. 22, 2005

(54) METHOD AND APPARATUS FOR REQUESTING AND DISPLAYING WORKLIST DATA FROM REMOTELY LOCATED DEVICE

(75) Inventors: Charles C. Brackett, Waukesha, WI (US); Gregory C. Stratton, Wauwatosa, WI (US); Takao Shiibashi, Brookfield, WI (US)

(73) Assignee: General Electric Company, Waukesha, WI (US)

( * ) Notice: Subject to any disclaimer, the term of this patent is extended or adjusted under 35 U.S.C. 154(b) by 0 days.

(21) Appl. No.: 09/302,080

(22) Filed: Apr. 28, 1999

(51) Int. Cl.[7] .......................... G06F 15/00; G06F 17/30
(52) U.S. Cl. .......................... 358/1.15; 358/1.9; 707/1; 707/104.1; 345/739
(58) Field of Search .................... 345/733, 734, 345/736, 738, 739; 358/1.15, 1.9, 1.16, 1.18, 402, 403; 707/1, 3, 4, 5, 102, 104.1; 709/204, 206, 207

(56) References Cited

U.S. PATENT DOCUMENTS

| | | | | |
|---|---|---|---|---|
| 5,325,293 A | * | 6/1994 | Dorne | 705/2 |
| 5,452,416 A | * | 9/1995 | Hilton et al. | 345/783 |
| 5,483,624 A | * | 1/1996 | Christopher et al. | 358/1.18 |
| 5,851,186 A | * | 12/1998 | Wood et al. | 600/437 |
| 5,870,549 A | * | 2/1999 | Bobo, II | 709/206 |
| 5,897,498 A | | 4/1999 | Canfield et al. | 600/437 |
| 5,920,317 A | * | 7/1999 | McDonald | 345/853 |
| 5,974,430 A | * | 10/1999 | Mutschler, III et al. | 715/505 |
| 5,997,478 A | * | 12/1999 | Jackson et al. | 600/437 |
| 6,574,629 B1 | * | 6/2003 | Cooke, Jr. et al. | 707/10 |
| 6,674,449 B1 | * | 1/2004 | Banks et al. | 345/740 |

* cited by examiner

Primary Examiner—Joseph R. Pokrzywa
(74) Attorney, Agent, or Firm—Ostrager Chong Flaherty & Broitman P.C.

(57) ABSTRACT

A computerized imager is programmed with software that enables an efficient worklist query to be sent to a remotely located device. A user-interactive menu is provided which allows the user to select one or more search fields and enter search criteria for each field. The search is initiated by clicking on a virtual representation of a Search key on the worklist menu. The software also allows the system operator to control which data in the retrieved worklist data is displayed on the worklist menu. The system user can transfer the information in any entry on the retrieved worklist to the new patient menu by simply clicking on that entry. That information will be included with each image stored in image files on the hard disk for that job.

10 Claims, 6 Drawing Sheets

Worklist Setup

| Display Order | Search Field | Criteria |
|---|---|---|
| DISPLAY 1 | First Name | |
| DISPLAY 2 | Last Name | |
| DISPLAY 4 | Exam Start Date | 3/10/1999 — 68 |
| SEARCH | Exam Start Date Range | 9 days |
| SEARCH | Modality | |
| SEARCH | Schedule Description | |
| SEARCH | Station Name | |
| SEARCH | Location | |
| SEARCH | Request Procedure ID | |
| SEARCH | Accession Number | |
| SEARCH | Admission ID | |
| SEARCH | AE Title | |
| DISPLAY 3 | Patient ID | |
| SEARCH | Date of Birth | 0/0/1 0 |
| SEARCH | Gender | |
| SEARCH | Req. Proc. Desc. | |

FIRST NAME   LAST NAME   PATIENT ID   START DATE

TKBL/RET to position   SET to select   ROI Size to page
                                        EXIT to save

FIG. 5

|  | Worklist | Page 1 of 1 | |
|---|---|---|---|
| FIRST NAME 70 | LAST NAME | PATIENT ID | START DATE 03/10/1999 |
| HUGO | VERMICELLI | 99-123004 | 03/09/1999 |
| SAMUEL | ADAMS | 27 | 03/19/1999 |

SEARCH   CLEAR

TKBL to position    SET to select    ROI Size to page / EXIT to quit

FIG.6

METHOD AND APPARATUS FOR REQUESTING AND DISPLAYING WORKLIST DATA FROM REMOTELY LOCATED DEVICE

FIELD OF THE INVENTION

This invention generally relates to imaging systems used in medical diagnostics. In particular, the invention relates to the retrieval of worklist data from a worklist broker via a network.

BACKGROUND OF THE INVENTION

In addition to storing images internally, modern ultrasound imaging systems need to be able to transfer images to various types of remote devices via a communications network. To successfully transfer images, the relevant networking features of the ultrasound imager must be compatible with the networking features of the destination remote device. In particular, the ultrasound imager must place the data to be transferred in a format which can be handled by the destination remote device. An attempt to accomplish the foregoing is the adoption of the DICOM (Digital Imaging and Communications in Medicine) standards, which specify the conformance requirements for the relevant networking features. The DICOM standards are intended for use in communicating medical digital images among printers, workstations, acquisition modules (such as an ultrasound imaging system) and file servers. The acquisition module is programmed to transfer data in a format which complies with the DICOM standards, while the receiving device is programmed to receive data which has been formatted in compliance with those same DICOM standards.

DICOM involves more than digital image transfer. DICOM functionality includes the following Service Classes: archive/transfer images: store (across network); archive/interchange images: media storage; query for information and retrieve images; make image hard copies: print management; patient, study and results management; radiology information system modality: worklist management; and test connectivity: verification. A fundamental concept employed in DICOM is "Services on Objects". One example of an "Object" is an ultrasound image. Two examples of a "Service" are the "Store" and "Query/Retrieve" functions. In DICOM, methods of operating on information objects are referred to as "Service Object Pair Classes" (SOP Classes). Examples of SOP Classes are "Store an ultrasound image", "Print an ultrasound image", "Find which studies there are for a certain patient", "Retrieve all studies of a certain patient" and "Retrieve a worklist". Unique Identifiers (UIDs) are defined for all SOP Classes. UIDs are also given to all studies, series and images. These UIDs are, for instance, used for retrieval. In the DICOM vernacular, a patient has a study which comprises a study component, e.g., examination using a particular modality. Images acquired in sequence in the course of a study on a patient form a series of objects.

The DICOM system is based on the client/server concept. The device which uses a service (on objects) is the client device, while the device which provides the service is the server device. The client device is referred to as a Service Class User (SCU), while the server device is referred to as a Service Class Provider (SCP). The SCU sends a Service Request to the SCP over a local area network (LAN). The SCP sends back a response to the SCU over the same LAN. If the response is affirmative and a communications syntax is agreed upon, an association between the SCU and the SCP is opened and data can be transferred between the two devices. In the DICOM system a device is not limited to one role: it can be both SCU and SCP at different times.

The DICOM system is designed to facilitate the communication of digital images of different types, e.g., X-ray, computerized tomography, magnetic resonance and ultrasound imaging. In an ultrasound imager having conventional DICOM capability, three local real-world activities occur: Image Send, Image Print and Remote Verification. Image Send and Image Print can be done in either automatic or manual mode. Verification of remote DICOM devices configured on the ultrasound imager is performed when the imager is powered up or when requested by the system operator.

All DICOM activities are handled in a queued manner by application software running on a host computer incorporated in the imager. In one type of ultrasound imager, the user can select any image in cine memory to be sent in DICOM format via a LAN to a remote device having DICOM capability. The host computer of the ultrasound imaging system is programmed with DICOM system software which facilitates transmission of image frames from the cine memory to the remote DICOM device via the host computer hard disk and the LAN.

In the conventional ultrasound imager, Image Send can be used in automatic or manual mode, depending on the user configuration. When automatic mode is configured, console keys are used to capture the image and to store it on the hard disk. The request is queued to a DICOM queue manager (preferably implemented in software), which requests an association with the destination remote device. After the association with the remote device has been opened, the queue manager "pushes" the image to the remote device without user intervention. The transfer is done in the background while scanning or other operator activities continue. In manual mode, the captured images are archived on the hard disk or on a MOD during the exam(s). Upon completion of the exam(s) the images are tagged using an archive menu and queued to any of the network devices that have been configured on the imager. The images are sent sequentially in the background while scanning or other operator activities proceed. Image Print works much the same way as Image Send, in both automatic and manual modes, the only difference being that the destination device is a printer.

In order to accomplish image transfer, the ultrasound imaging system must know the configuration of the destination remote device prior to attempting to communicate with that device. The configuration data for the destination remote device is typically inputted to the ultrasound imager during software installation by a field engineer, although the DICOM network can be configured at any time. When the imager receives an instruction to transmit data to a particular remote device from the system operator, the imager software converts the image data to be transferred into the DICOM format required by the destination remote device, based on the configuration data for that device stored in system memory. The imager also sends a request over the network to the destination remote device to open an association, i.e., to connect the imager to the destination remote device. If the remote device responds in the affirmative, the imager and remote device then agree on which SOP Class is to be used and which device will act as the server and which as the client. The ultrasound imager also selects the appropriate encoding syntax from those accepted by the remote device. Other communication parameters are also negotiated.

After the DICOM communications protocol has been settled, the association is opened and the imager attempts to send the DICOM-formatted image frame (object) to the remote device via the network. The transfer is done in the background while scanning or other operator activities continue. If the remote device is a storage device, each image frame is transferred singly in response to a Send request inputted by the operator., The conventional imager with DICOM capability will open an association with a storage device in response to each "send to a storage device" instruction. If a transfer is successful, the association for that transfer is immediately closed. If the remote device is a printer configured to print multi-image film, then a number of images are accumulated to make up a multi-image film and an association is opened in response to a Send instruction when a number of images sufficient to fill the multi-image film have been accumulated. After the full film session of images has been transmitted, the association between the imager and printer is closed.

If the destination remote device sends back a message indicating successful receipt of the transmitted data, the DICOM-formatted image frame can be deleted from the imager memory. Alternatively, the system operator can instruct the imager to retain the DICOM-formatted image frame on the imager hard disk or to store it on a MOD inserted in the imager.

In addition to the digitized image (i.e., pixel data), the DICOM object transferred from the ultrasound imager also includes attribute information. For example, the attribute information may include patient attributes (e.g., patient name and patient identification number), study attributes (e.g., accession number and study date), series attributes (e.g., modality type and series date), and image attributes (e.g., image type and numbers of rows and columns). Each attribute has a name, a value representation and a tag. A tag is a four-byte number (e.g., in hexadecimal code) unique to the attribute. The value representation defines what type of value it can have (e.g., a 64-character string, binary data, etc.).

In accordance with DICOM standards, there are three types of attributes. Type 1 comprises attributes which are mandatory and must always be present with a value; Type 2 comprises attributes which are mandatory but are allowed to be empty; and Type 3 comprises attributes which are optional and are also allowed to be empty. An incompatibility between two devices may arise, for example, if the receiving device requires that a Type 3 attribute be transmitted while the sending device does not include that attribute in its transmission. As a result, even if both devices are configured in accordance with current DICOM standards, the data transfer cannot occur. Thus, even mutual conformance to DICOM standards does not guarantee that two devices can be compatibly connected to each other.

In accordance with a further aspect of the DICOM system as currently implemented, an ultrasound imaging system can retrieve a worklist from a Radiology Information System (RIS) at a hospital via the LAN. The retrieved worklist may, e.g., comprise all patients to be examined on a particular day using that particular ultrasound imager. The worklist includes the following information for each patient: name, identification number, sex, birth date, accession number, study data, etc. The information retrieval is initiated by the ultrasound imager. In response to this query, the RIS transmits the worklist to the ultrasound imager, which stores it in memory. This worklist is then available for viewing by the sonographer. The patient currently being examined can be selected from the worklist.

Because the DICOM capability is implemented in software, these features of the ultrasound imaging system can be readily upgraded. One goal of such upgrades is to increase the efficiency of the system operator by making the system simpler to operate, e.g., by requiring fewer manipulations to activate a particular operation. Another goal of system upgrades is to increase the ability of the imager to connect rapidly, efficiently and reliably to remote devices on the network, i.e., to increase connectivity.

SUMMARY OF THE INVENTION

The present invention is a computerized imager which is programmed to send an efficient modality worklist query to a remotely located device, e.g., a worklist broker. In accordance with the preferred embodiment of the invention, a user-interactive Worklist Setup menu is provided which allows the user to select one or more search fields and enter search criteria for each field. The Worklist Setup menu also allows the system operator to control which data in the retrieved worklist data will be displayed on a user-interactive Worklist menu. The search is initiated by clicking on a virtual representation of a Search key on the Worklist menu. The search results are received from the remote worklist broker by the imaging system and stored in memory. The search fields designated for display are displayed on the Worklist menu. The system user can transfer all information for any entry displayed on the Worklist to the new patient menu by simply clicking on that entry.

The invention gives the system user the ability to create a local patient list on the imaging system. That local patient list can be viewed on the Worklist menu. The user can select any patient from the worklist for an examination. Selecting a patient from the worklist means that all of the data associated with that patient, which was retrieved from the worklist broker (remote device), will be included with every image of that patient which is stored in image files on the hard disk. Those images are subsequently converted into DICOM objects for transfer to remote printers and storage devices.

The invention also gives the user optimal flexibility in scoping worklist queries to include only necessary data. This reduces information overload and optimizes machine efficiency.

Although the preferred embodiment of the invention is disclosed in the context of imaging systems which communicate with remote devices using the DICOM standard, it will be appreciated that the broad concept of the invention has application with any digital image communications standard or protocol that provides for construction of worklists.

DETAILED DESCRIPTION OF THE PREFERRED EMBODIMENTS

Figure 1:
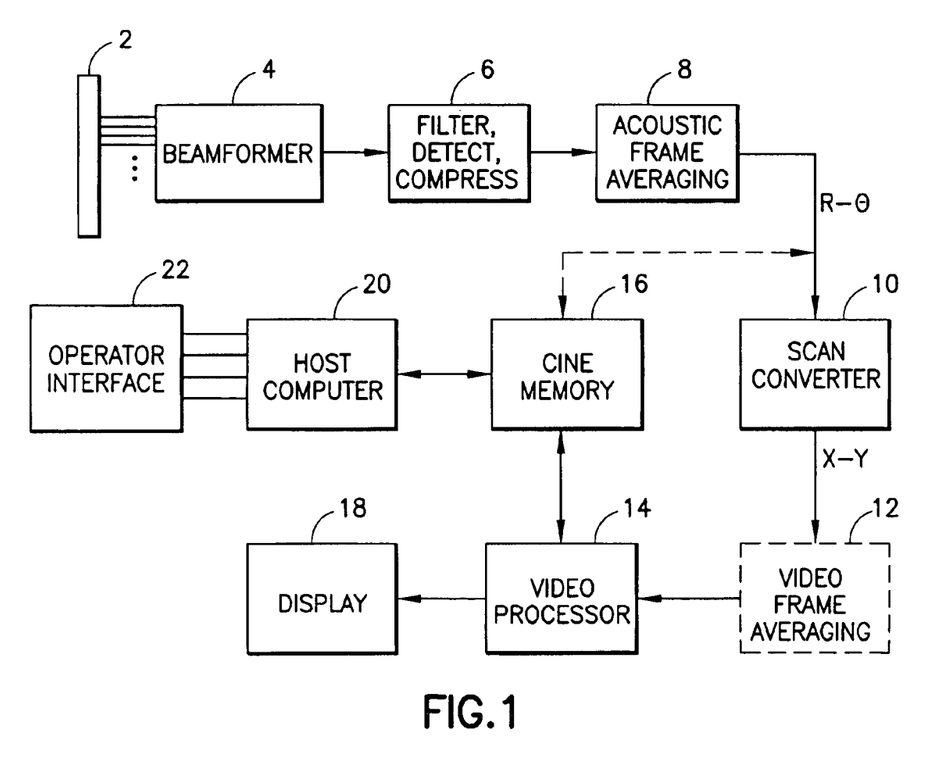
FIG. 1 is a block diagram showing a conventional ultrasound imaging system of the type which can be programmed to have DICOM capability.

FIG. 1 shows a conventional computerized ultrasound imaging system which can be programmed to communicate with remote devices over a network in conformance with the DICOM standard. The type of imaging system depicted in FIG. 1 creates two-dimensional B-mode images of tissue in which the brightness of a pixel is based on the intensity of the echo return. The basic signal processing chain is as follows.

An ultrasound transducer array 2 is activated to by a transmitter in a beamformer 4 to transmit an acoustic burst which is focused at a point along a scan line. The return RF signals are detected by the transducer elements and then dynamically focused to form a receive beam by a receiver in the beamformer 4. The receive beamformer output data (I/Q or RF) for each scan line is passed through a B-mode processing chain 6, which preferably includes demodulation, filtering, envelope detection, logarithmic compression and edge enhancement.

Depending on the scan geometry, up to a few hundred receive vectors may be used to form a single acoustic image frame. To smooth the temporal transition from one acoustic frame to the next, some acoustic frame averaging 8 may be performed before scan conversion. In general, the log-compressed display data is converted by the scan converter 10 into X-Y format for video display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which maps the video data using a gray-scale mapping. The gray-scaled image frames are then sent to a video monitor 18 for display.

System control is centered in a host computer 20, which accepts operator inputs through an operator interface 22 and in turn controls the various subsystems. (In FIG. 1, only the image data transfer paths are depicted.) The operator interface comprises a keyboard, a trackball, a multiplicity of push-buttons, and other input devices such as sliding and rotary knobs.

During imaging, a long sequence of the most recent images are stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed via trackball control, and a section of the image loop can be selected for hard disk storage.

For an ultrasound imaging system which has been configured with a free-hand three-dimensional imaging capability, the selected image sequence stored in cine memory 16 is transferred to the host computer 20 for three-dimensional reconstruction. The result is written back into another portion of the cine memory, from where it is sent to the display system 18 via video processor 14.

Figure 2:
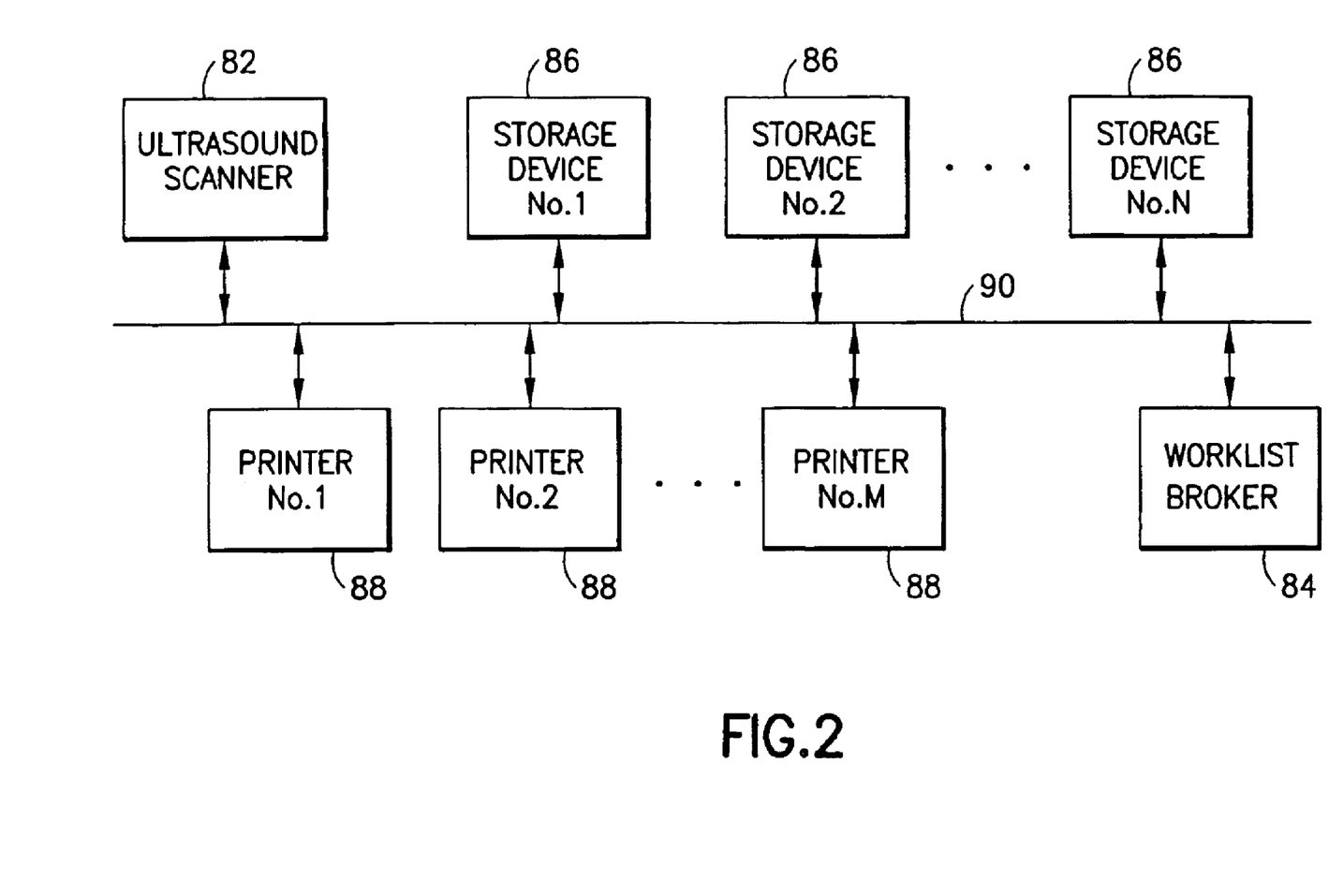
FIG. 2 is a block diagram showing a typical DICOM network.

FIG. 2 generally depicts a simplified DICOM network having an ultrasound scanner 82, a worklist broker (e.g., an RIS) 84, N storage devices 86, and M printing devices 88, all connected to a LAN 90. It will be readily appreciated that this diagram represents a simplified example of a DICOM network and that an actual DICOM network in the real world will have many more devices connected to the LAN, including modalities other than ultrasound imaging systems. The present invention is incorporated in an ultrasound imager (scanner) having the built-in capability to communicate with any one or more of the devices 84, 86 and 88 in conformance with the DICOM requirements.

Figure 3:
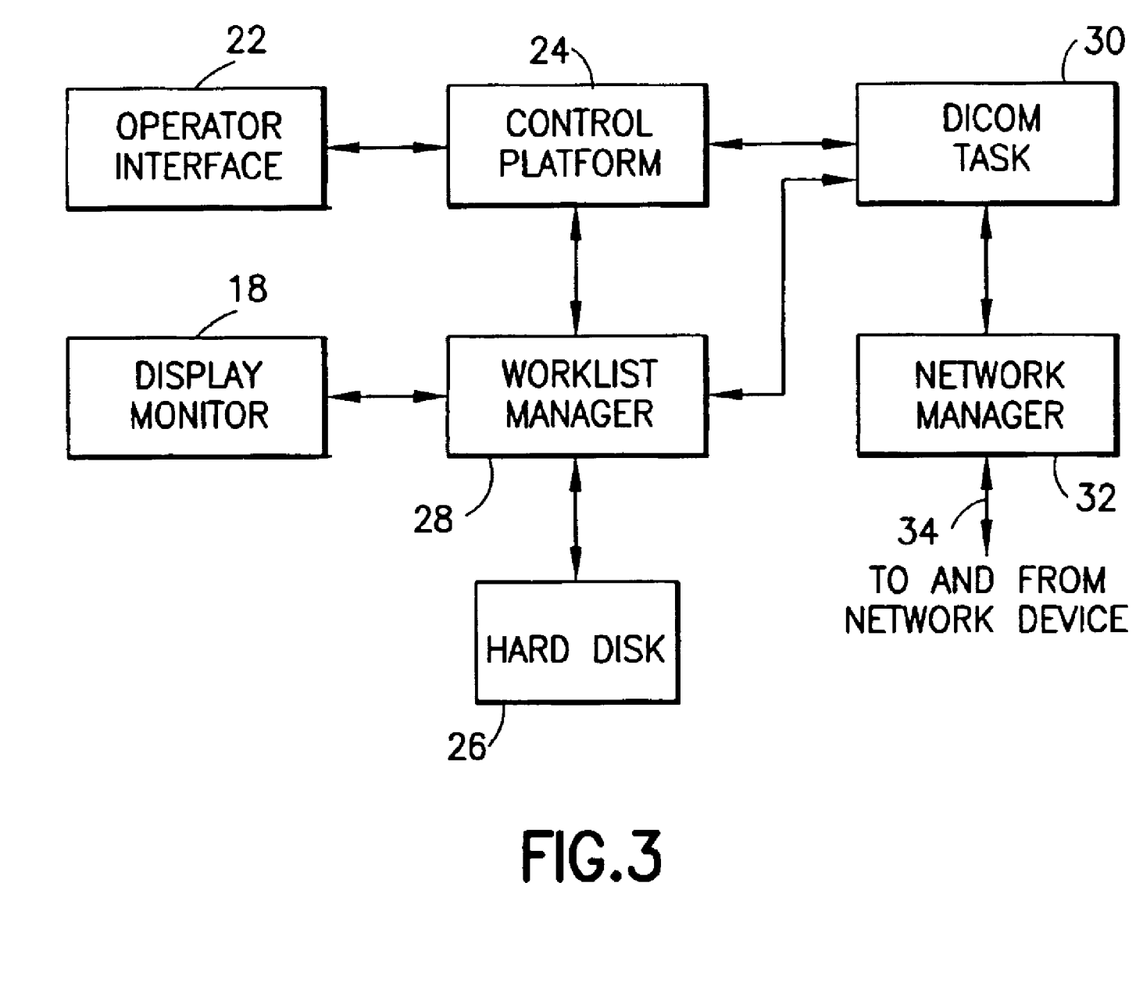
FIG. 3 is a block diagram generally depicting the hardware and software of a portion of an ultrasound imaging system in accordance with the preferred embodiment of the present invention.

A portion of such an ultrasound imager is generally depicted in FIG. 3. At the outset it should be appreciated that all of the blocks depicted in FIG. 3, with the exception of the display screen 18 and the operator interface 22, are preferably incorporated in the host computer (depicted in FIG. 1 as block 20). It should be further appreciated that blocks 24, 28, 30 and 32 in FIG. 3 are preferably implemented as software.

In accordance with the preferred embodiments of the invention, commands inputted via the operator interface 22 are detected and processed by a control platform 24. In return, the control platform will provide signals to the operator interface which activate various visual indicators on the operator interface to indicate the status of various functions. In response to manipulation of the appropriate key or appropriate set of keys by the operator, a worklist manager 28 will display operator-interactive menus, such as the Worklist Setup and Worklist menus (shown in FIGS. 5 and 6, respectively) on the display monitor 18. Each menu includes fields for data entry and settable fields which can be set to a desired state by highlighting that field using a trackball and then pressing the Set key on the operator interface.

The operator inputs to the Worklist Setup and Worklist menus are received by worklist manager 28 via the control platform 24. When the operator initiates a search, the control platform 24 sends a Worklist Query" posting to the appropriate DICOM task 30, i.e., the DICOM task configured to perform modality worklist queries. The worklist DICOM task 30 then requests the worklist setup data from the worklist manager 28. The worklist DICOM task 30 constructs a worklist query in the format required by the destination worklist broker (e.g., 84 in FIG. 2) and then sends that worklist query to the network via the network manager 32 and port 34, accompanied by a destination address.

In response to initiation of a modality worklist query, the DICOM task will open a connection (association) to the destination worklist broker and negotiate a syntax. In particular, the DICOM task 30 sends a request via the network manager 32 and a port 44 that an association with the configured worklist broker be opened. If the worklist broker responds affirmatively and if a communications syntax is agreed upon, the association is opened. Once the association is open and assuming that a channel on the network is available (i.e., the network is not busy), the worklist query is sent from the imager onto the network via the network manager 32 and the port 34. If the destination worklist broker sends back the requested worklist information, then the DICOM task 30 passes that information on to the worklist manager 28, which in turn stores it on the hard disk 26 and displays the information on the Worklist menu.

Figure 4:
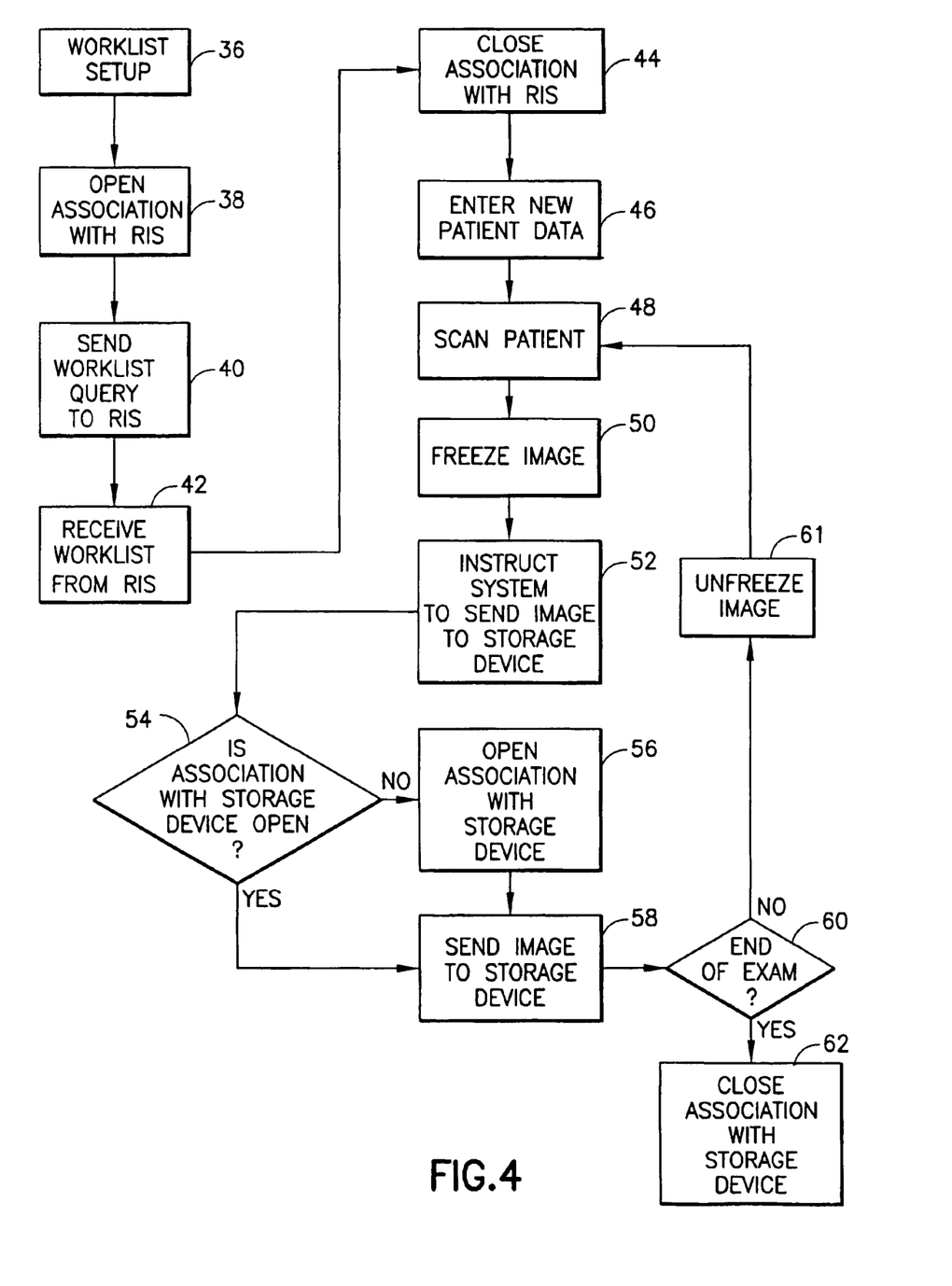
FIG. 4 is a flowchart depicting a procedure for retrieving a worklist from one remotely located device, performing an examination listed on that worklist, and sending examination images to another remotely located device.

A worklist query is typically made by the system operator prior to initiation of an examination. One purpose of such a query is to retrieve patient information from a central location and annex that information to each image frozen and stored on the hard disk (26 in FIG. 3). In accordance with the preferred embodiment of the invention, the system user configures the system to request only selected worklist information from the central location. Referring to FIG. 4, the system operator sets up the worklist (step 36) and defines the search parameters by interacting with the Worklist Setup menu shown in FIG. 5. After the worklist has been set up and the search parameters defined, the operator initiates a search by clicking on a Search field 74 on the Worklist menu (shown in FIG. 6), which is retrieved via a New Patient menu (not shown). (As used herein, the term "clicking" includes, but is not limited to highlighting a field by manipulation of a trackball and then pressing a Set key on the operator interface.) The DICOM task 30 (see FIG. 3) then opens up an association with the RIS or other worklist broker (step 38) and sends the worklist query over the network (step 40). The imager subsequently receives the requested worklist information from the remote worklist broker (step 42). If the transfer of worklist information from the remote worklist broker to the imaging system was successful, the association is then closed (step 44). The operator can then click on a particular entry in the worklist displayed on the Worklist menu, in response to which all retrieved information for that worklist entry is automatically entered into a new patient data file (step 46). The new patient data can be viewed by returning to the New Patient menu on the display screen. When the user exits the New Patient menu, a DICOM Study Instance UID is created. This Study Instance UID forms the base of the SOP Instance UID which tells the receiving DICOM printer or storage device (SCP) that the image received belongs to a particular patient. Every image taken by the user, after exiting the "New Patient" menu, will have the same UID.

The examination may then begin. The user will scan the patient (step 48), as needed. The user, at any time, can freeze the image (step 50) and take a snapshot of that image to send to a storage device (step 52). The SOP Instance UID will direct the image to the proper patient's folder of images. Storage devices receive images one at a time. The typical method of image transfer to a storage device is as follows: the queue manager opens an association (connection) with the receiving storage device; transfer negotiations occur; the image is transferred; and the association is closed. Alternatively, the system can be configured to open the association once and keep it open throughout the entire exam. In this case, the association is opened upon the sending of the first image. Now, all images selected to be sent after the association has been opened, and before the "End Exam" button is pushed, will be transferred during that one association. No other associations need to be made, thereby increasing transfer efficiency.

Referring again to FIG. 4, in response to each depression of a Print/Store button configured to the destination storage device, the DICOM task associated with that storage device (which task is different than the worklist DICOM task depicted in FIG. 3) will determine if the association with that storage device is open (step 54). If not, the storage DICOM task will open the association (step 56), as previously described. If the association is already open, then the storage DICOM task will attempt to send the DICOM object to the storage device. If the network is busy and the DICOM object cannot be sent, the DICOM object will remain queued and succeeding images will also be queued during this time. If the network will allow the DICOM object to be sent to the destination storage device, then the DICOM object constructed by the DICOM task will be transmitted to the storage device via the DICOM network (step 58). The queue manager then determines whether the "End Exam" button has been pressed (step 60). If it has, the queue manager instructs all open DICOM tasks to close any associations (step 62). If the "End Exam" button has not been depressed, the association will not be closed, and the system operator can again scan the patient after unfreezing the image (step 61).

Although FIG. 3 depicts only one DICOM task, in accordance with the preferred embodiment of the invention, the imager is programmed with multiple DICOM tasks. In the preferred embodiment, one DICOM task (32 in FIG. 3) is dedicated to sending worklist queries and ten DICOM tasks can be configured to convert image files into either print or storage objects.

In accordance with the preferred embodiment, the host computer of the imager is programmed to store in memory configuration data input via a Device Configuration menu (not shown) for the remote worklist broker to be queried. Although the system can store configuration data for multiple worklist brokers, the system is programmed so that only one configured worklist broker at a time can be activated. When a particular worklist broker is activated (e.g., by clicking on an activation field on the corresponding page of the Device Configuration menu), the DICOM task 30 (FIG. 3) is configured in accordance with the configuration data for that particular worklist broker.

In accordance with the preferred embodiment of the invention, a user-interactive Worklist Setup menu (shown in FIG. 5) is provided which allows the user to select one or more search fields and enter search criteria for each field. The Worklist Setup menu also allows the system operator to control which data in the retrieved worklist data will be displayed on a user-interactive Worklist menu.

Figure 5:
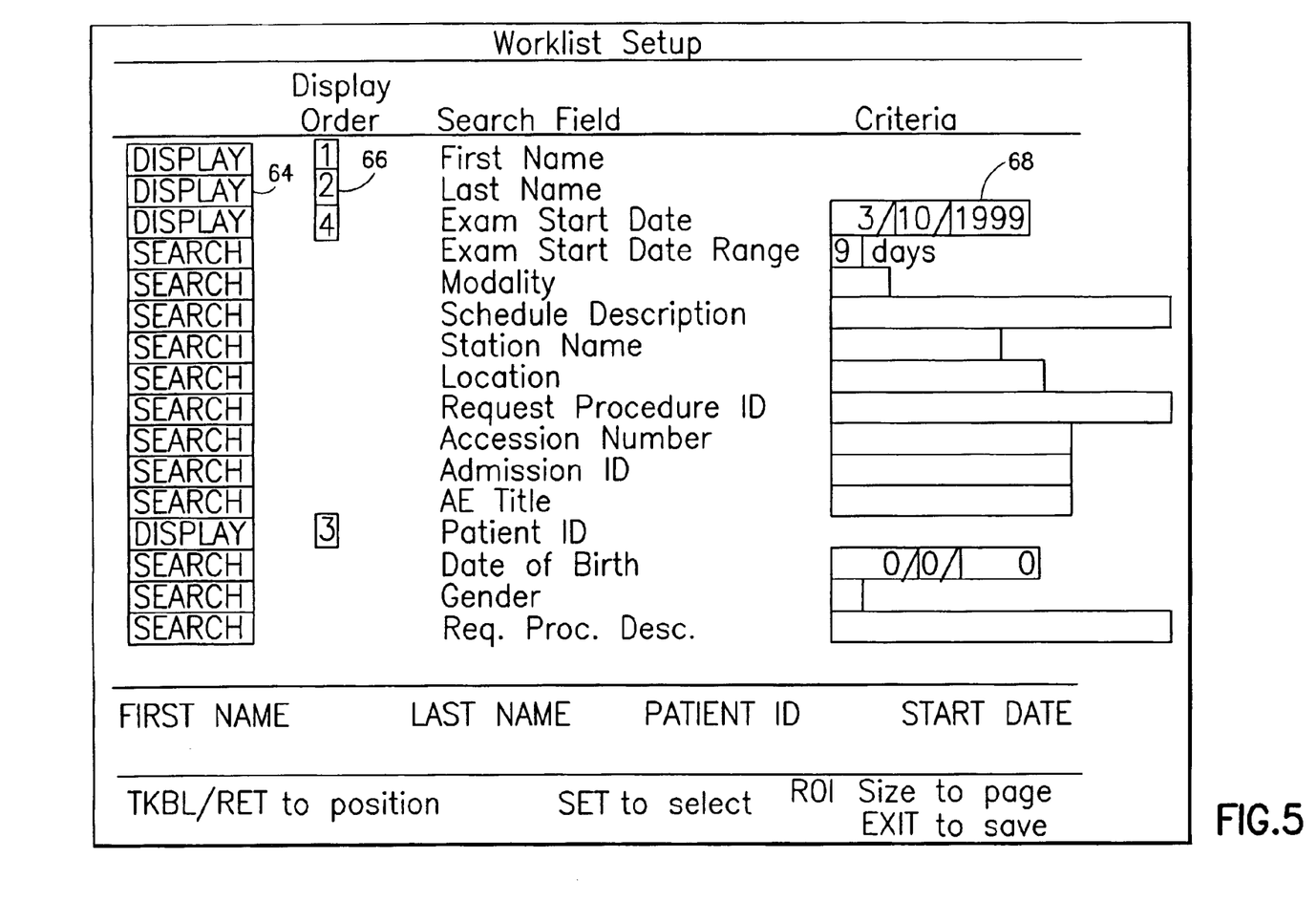
FIG. 5 is a schematic reproducing a Worklist Setup display menu which the operator interacts with during setup of a worklist query in accordance with the preferred embodiment of the invention.

Referring to FIG. 5, the Worklist Setup menu comprises a list of search fields. The first column 64 on this page comprises a toggle field for each search field. When the user highlights a toggle field using the trackball and presses the Set key on the keyboard, the user may toggle through three states. Those states are Ignore, Display and Search (only two of which are represented FIG. 5). The Ignore state means that the associated search field should be ignored as a query. If the Ignore state is selected, the trackball will take the user to the next line. The Display state defines the associated search field as "search and display" when submitting a query. If the Display state is selected, the trackball will take the user to the Display Order column 66, so that the user may choose the order in which this item will appear on the Worklist menu. The Search state defines the associated search field as "search", but do not display, when submitting a query. If the Search state is selected, the trackball will take the user to the corresponding Criteria field 68 to define that parameter of the search. In the example depicted in FIG. 5, the worklist query has been setup to search for all jobs scheduled in the time period from nine days before to nine days after Mar. 10, 1999, the entry in the Exam Start Date field 68. In addition, the headings for the Worklist menu, duplicated in the lower portion of the Worklist Setup menu, are displayed in the order determined by the entries in the Display Order fields 66.

Figure 6:
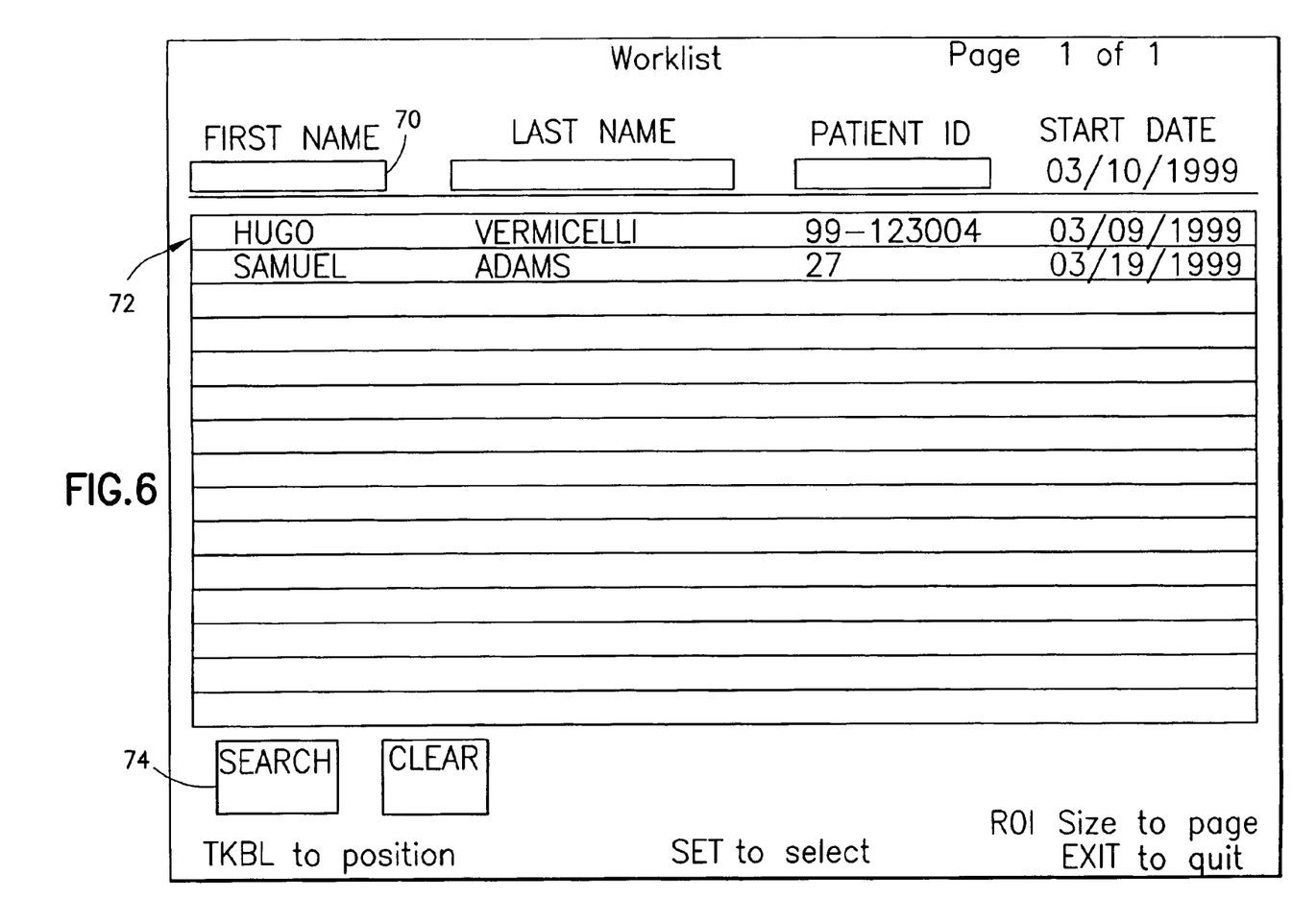
FIG. 6 is a schematic reproducing a Worklist display menu which the operator interacts with to initiate a worklist query and later select entries from the retrieved worklist in accordance with the preferred embodiment of the invention.

After setting up the Worklist, the user returns to the New Patient menu and then uses an ROI Size button to page to the Worklist menu, which is depicted in FIG. 6. The Worklist menu is used to perform a query on the configured and activated worklist broker. When the Worklist menu appears on the display screen, the user may enter text in the allowable fields 70 for querying. For example, the user may enter a specific patient ID to query the remote worklist broker for any job scheduled within the searched time window for the patient identified. The search is initiated by clicking on a virtual representation 74 of a Search key. The query results will be displayed in fields 72 under the respective displayed headings. The query results are also sent to the worklist manager and then stored on the hard disk.

The displayed search fields are dynamically placed onto the screen depending on what the user has defined in the Worklist Setup menu. If the user has marked the search fields to be "Search", then the search criteria will only appear on the Worklist Setup menu. If the user has marked the search fields to be "Display", then those search fields will appear in columns near the top of the Worklist menu, directly above query fields 70 for the user to enter a desired query. The search fields designated for display are displayed on the Worklist menu. The system user can transfer all information for any entry displayed on the Worklist menu to the new patient menu by simply clicking on that entry. That information will be included with each image stored in image files on the hard disk for that job.

Referring to FIG. 3, the search and display parameters entered on the Worklist Setup and Worklist menus via the operator interface are processed by the worklist manager 28. The search parameters are passed on to the DICOM task 30, while the worklist manager 28 uses the display parameters to set up the Worklist menu. In response to a search initiation posting from the control platform, the DICOM task 30 formulates a query based on the search parameters and then sends it to the network manager 32. When the search results are later received from the remote worklist broker via the network manager, the DICOM task passes those search results on to the worklist manager 28. The worklist manager then stores the retrieved worklist data on the hard disk 26 and displays on the display screen those entries corresponding to search fields designated for display, each entry being placed under the column heading to which it belongs.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A scanner comprising:
   an operator interface;
   a display monitor;
   a scanning subsystem for acquiring data representing an image of a target object;
   a networking port for communicating with a network; and
   a computer programmed to perform the following steps:
   (a) controlling said display monitor to display a screen comprising a list of searchable parameters, each listed searchable parameter being associated with a respective toggle field and a respective fillable search criteria field, each toggle field having three possible states, any one of said three states being selectable by a user using said operator interface, a first toggle state indicating that the respective searchable parameter will be ignored during a search in a database, a second toggle state indicating that the respective searchable parameter will be employed as a search parameter during the search but that a retrieved value for that searchable parameter will not be displayed in a display of worklist search results, and a third toggle state indicating that the respective searchable parameter will be employed as a search parameter during the search and that a retrieved value for that searchable parameter will be displayed in a display of worklist search results;
   (b) formulating a worklist search request message as a function of the search parameters having toggle fields in said second or third toggle state in response to input of a search command using said operator interface;
   (c) opening an association with a remote worklist broker via said network;
   (d) sending said worklist search request message to the remote worklist broker via said networking port while said association is open;
   (e) controlling said display monitor to display at least those portions of the worklist search results received from the remote worklist broker in response to step (d) representing retrieved values for those searchable parameters designated for display by said third toggle state;
   (f) registering portions of said worklist search results belonging to a particular patient in response to input of a patient selection command using said operator interface after step (e);
   (g) controlling said scanning subsystem to acquire an image in response to input of a scan command using said operator interface after step (f); and
   (h) storing said acquired image in association with said registered portions of said worklist search results in response to input of a save command using said operator interface.

2. The scanner as recited in claim 1, wherein said computer is further programmed to control said display monitor to display said acquired image.

3. The scanner as recited in claim 1, wherein said screen further comprises fields that can be filled with worklist display order instructions inputted using said operator interface, said worklist display order instructions indicating the order in which said items should be displayed on said display monitor in step (e).

4. The scanner as recited in claim 1, wherein said registering step comprises automatically entering said portions of said worklist search results belonging to said particular patient menu into a new patient data file.

5. The scanner as recited in claim 1, wherein said worklist search request message is formatted in accordance with DICOM protocol.

6. The scanner as recited in claim 1, wherein said scanning subsystem comprises a multiplicity of ultrasound transducer elements.

7. A system comprising a network, scanner connected to said network, and a worklist broker connected to said network, wherein said worklist broker comprises means for retrieving stored patient information from a database in response to a worklist search request message received via said network, and wherein said scanner comprises an operator interface, a display monitor, a scanning subsystem for acquiring data representing an image of a target object, a hard disk, and a computer programmed to perform the following steps:

(a) controlling said display monitor to display a screen comprising a list of searchable parameters, each listed searchable parameter being associated with a respective toggle field and a respective fillable search criteria field, each toggle field having three possible states, any one of said three states being selectable by a user using said operator interface, a first toggle state indicating that the respective searchable parameter will be ignored during a search in a database, a second toggle state indicating that the respective searchable parameter will be employed as a search parameter during the search but that a retrieved value for that searchable parameter will not be displayed in a display of worklist search results, and a third toggle state indicating that the respective searchable parameter will be employed as a search parameter during the search and that a retrieved value for that searchable parameter will be displayed in a display of worklist search results;

(b) formulating said worklist search request message as a function of the search parameters having toggle fields in said second or third toggle state in response to input of a search command using said operator interface;

(c) opening an association with said remote worklist broker via said network;

(d) sending said worklist search request message to the remote worklist broker via said network while said association is open;

(e) controlling said display monitor to display at least those portions of the worklist search results received from the remote worklist broker in response to step (d) representing retrieved values for those searchable parameters designated for display by said third toggle state;

(f) registering portions of said worklist search results belonging to a particular patient in response to input of a patient selection command via said operator interface after step (e);

(g) controlling said scanning subsystem to acquire an image in response to input of a scan command via said operator interface after step (f); and (h) storing said acquired image on said hard disk in association with said registered portions of said worklist search results in response to input of a save command via said operator interface.

8. The system as recited in claim 7, further comprising a storage device connected to said network, wherein said computer is further programmed to perform the following steps:

(i) opening an association with said storage device via said network; and (j) sending a file comprising said acquired image and said associated portions of said worklist search results to said storage device via said network in response to input of a store command via said operator interface while said association is open.

9. The system as recited in claim 8, wherein said worklist search request message and said file for storage are formatted in accordance with DICOM protocol.

10. The system as recited in claim 7, wherein said scanning subsystem comprises a multiplicity of ultrasound transducer elements.

* * * * *